(12) United States Patent
Wang et al.

(10) Patent No.: US 8,974,548 B2
(45) Date of Patent: Mar. 10, 2015

(54) HAIR COMPOSITION

(71) Applicant: Conopco, Inc., Englewood Cliffs, NJ (US)

(72) Inventors: Jinfang Wang, Shanghai (CN); Xiaoxia Yang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/346,085

(22) PCT Filed: Sep. 24, 2012

(86) PCT No.: PCT/EP2012/068744
§ 371 (c)(1),
(2) Date: Mar. 20, 2014

(87) PCT Pub. No.: WO2013/045382
PCT Pub. Date: Apr. 4, 2013

(65) Prior Publication Data
US 2014/0230162 A1    Aug. 21, 2014

(30) Foreign Application Priority Data

Sep. 26, 2011 (CN) .................. PCT/CN2011/001624

(51) Int. Cl.
| | | |
|---|---|---|
| *A61Q 5/10* | (2006.01) | |
| *A61K 8/35* | (2006.01) | |
| *A61K 8/41* | (2006.01) | |
| *A61K 8/46* | (2006.01) | |
| *A61Q 5/06* | (2006.01) | |

(52) U.S. Cl.
CPC ... *A61Q 5/10* (2013.01); *A61K 8/35* (2013.01); *A61K 8/416* (2013.01); *A61K 8/466* (2013.01); *A61Q 5/065* (2013.01)
USPC ................ 8/405; 8/581; 8/587; 8/588; 8/602; 8/606; 8/611; 8/632

(58) Field of Classification Search
USPC ............. 8/405, 581, 587, 588, 602, 606, 611, 8/632
See application file for complete search history.

(56) References Cited

U.S. PATENT DOCUMENTS

| | | |
|---|---|---|
| 4,293,543 A | 10/1981 | Cotte et al. |
| 4,385,049 A | 5/1983 | Cuca |
| 5,232,688 A | 8/1993 | Ziegler |
| 5,514,437 A | 5/1996 | Tanner |
| 5,612,044 A | 3/1997 | Suares |
| 5,645,822 A | 7/1997 | Meyere |
| 5,700,452 A | 12/1997 | Deckner |
| 5,705,145 A | 1/1998 | Miklean |
| 5,750,092 A | 5/1998 | Meyer |
| 5,756,075 A | 5/1998 | Meyer |
| 5,827,506 A | 10/1998 | McShane |
| 6,069,169 A | 5/2000 | Ptchelintsev |
| 6,231,837 B1 | 5/2001 | Stroud et al. |
| 6,423,326 B1 | 7/2002 | Shapiro |
| 6,616,918 B2 | 9/2003 | Candau |
| 6,645,474 B1 | 11/2003 | Galdi |
| 7,462,363 B2 | 12/2008 | Braun |
| 2002/0142018 A1 | 10/2002 | Scholz |
| 2003/0211069 A1 | 11/2003 | Deckner |
| 2004/0076597 A1 | 4/2004 | Berens |
| 2004/0185072 A1 | 9/2004 | Hitzel |
| 2004/0241113 A1 | 12/2004 | Stephens |
| 2005/0002978 A1 | 1/2005 | Crook |
| 2005/0089486 A1 | 4/2005 | Spindler |
| 2005/0238595 A1 | 10/2005 | Stella |
| 2007/0231355 A1 | 10/2007 | Quadir |
| 2007/0292373 A1 | 12/2007 | Russ |
| 2008/0124295 A1 | 5/2008 | Duranton |
| 2008/0317693 A1 | 12/2008 | Ricard |
| 2009/0041688 A1 | 2/2009 | Dueva-Koganov |
| 2010/0310483 A1 | 12/2010 | Klug |
| 2011/0129427 A1 | 6/2011 | Carnali |
| 2011/0305651 A1* | 12/2011 | Carnali et al. .................. 424/59 |
| 2012/0100083 A1 | 4/2012 | Carnali |
| 2014/0127150 A1 | 5/2014 | Braun |

FOREIGN PATENT DOCUMENTS

| | | |
|---|---|---|
| DE | 10049041 | 4/2002 |
| DE | 102004055541 A1 | 5/2006 |
| DE | 102008006857 | 1/2009 |
| EP | 1210933 A1 | 6/2002 |
| EP | 1579847 A1 | 9/2005 |
| GB | 953170 A | 3/1964 |
| JP | 2007246467 | 9/2007 |
| JP | 2007246467 A2 | 9/2007 |
| WO | WO9733560 | 9/1997 |

(Continued)

OTHER PUBLICATIONS

STIC Search Report dated Aug. 8, 2014.*
Zelikin et al., "A functionalizable Biomaterial based on Dihydroxyacetone, an Intermediate of Glucose Metabolism", Biomacromolecules, 2006, vol. 7, No. 11, pp. 3239-3244.
Bicker et al., "Catalytic conversion of carbohydrates in subcritical water: A new chemical process for lactic acid production", Journal of Molecular Catalysis A, 2005, vol. 239, No. 1-2, pp. 151-157.
Koizumi et al., "Hair dye for coloring head hair, is obtained by mixing silver salt and amino acid excluding cysteine and methionine, with hair dye cream base", Thomson Scientific, 2008.
PCT Interanational Search Report in PCT application PCT/EP2012/068744 dated Nov. 26, 2013 with Written Opinion.
IPER in PCT/EP2012/068744 dated Apr. 10, 2014.

(Continued)

*Primary Examiner* — Eisa Elhilo
(74) *Attorney, Agent, or Firm* — Ronald A. Koatz

(57) ABSTRACT

A hair coloring composition comprising: a) dihydroxyacetone or a derivative thereof; b) from 0.2 to 10 wt % of the total composition of a cationic conditioning compound c) a sulphonic compound of formula: $H_2N$—$(CHR^1)_p$ $S(-X)_q$—$Y$ in which where p is an integer from 1 to 5, $R^1$ is H or an alkyl group, X is O or S q is an integer from 0 or 1. Y is an alkyl group or hydroxyl group.

14 Claims, No Drawings

(56) References Cited

FOREIGN PATENT DOCUMENTS

| WO | WO0128552 A2 | 4/2001 |
|---|---|---|
| WO | WO03022235 | 3/2003 |
| WO | WO2005016302 | 2/2005 |
| WO | WO2006018149 A1 | 2/2006 |
| WO | WO2008013757 A2 | 1/2008 |
| WO | WO2009053287 A1 | 4/2009 |
| WO | WO2009074513 A1 | 6/2009 |
| WO | WO2011075871 A1 | 6/2011 |

OTHER PUBLICATIONS

Kohno et al., "Singlet Oxygen Quenching Activity of Hypotaurine", Nippon Keshohin Gijutsusha Kaishi, 1997, vol. 31, No. 4, pp. 455-460 (Abstract).

Kohno et al., "Singlet Oxygen Quenching Activity of Hypotaurine", Nippon Keshohin Gijutsusha Kaishi, 1997, vol. 31, No. 4, pp. 455-460.

PCT International Search Report in PCT/CN2010/000864 dated Mar. 24, 2011.

Written Opinion in PCT/CN2010/000864 dated Mar. 24, 2011.

\* cited by examiner

HAIR COMPOSITION

The present invention is directed to a composition and method for colouring the hair.

Conventional colouring compositions use oxidative coupling reactions to dye the hair, however there remains the need to develop colouring systems that do not use such colouring chemistry.

GB 953 170 discloses hair colouring compositions comprising dihydroxy acetone and glycine. We have found such compositions to be unstable on storage.

The hair colouring composition of the present invention mitigates the problem of poor stability and provides good colouring of hair from a hair colouring composition comprising dihydroxyacetone.

SUMMARY OF THE INVENTION

Accordingly the present application relates to a hair colouring composition comprising:
a) dihydroxyacetone (DHA) or a derivative thereof;
b) from 0.2 to 10 wt % of the total composition of a cationic conditioning compound;
c) a sulphonic compound of formula:

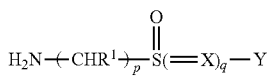

in which where p is an integer from 1 to 5,
$R^1$ is H or an alkyl group,
X is O or S
q is an integer from 0 or 1.
Y is an alkyl group or hydroxyl group.

The invention also relates to a method for colouring hair comprising the steps of applying to the hair a composition comprising dihydroxyacetone or a derivative and a sulphonic compound of formula:

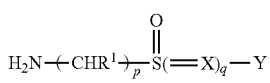

in which where p is an integer from 1 to 5,
$R^1$ is H or an alkyl group,
X is O or S
q is an integer from 0 or 1.
Y is an alkyl group or hydroxyl group.

DESCRIPTION OF THE INVENTION

Dihydroxyacetone

Compositions of the invention comprise dihydroxyacetone (DHA). Preferably the dihydroxyacetone is present from 0.05 to 35 wt % of the total composition, more preferably from 0.1 to 15 wt % most preferably from 0.5 to 10 wt %.

Sulphonic Acid Compound

Compositions of the invention comprise a sulphonic compound of formula:

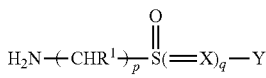

in which where p is an integer from 1 to 5,
$R^1$ is H or an alkyl group,
X is O or S
q is an integer from 0 or 1.
Y is an alkyl group or hydroxyl group.

Preferably the sulphonic acid compound or salt thereof is present from 0.05 to 35 wt % of the total composition, more preferably from 0.1 to 15 wt %, most preferably from 0.5 to 10 wt %.

In one preferred embodiment the composition of the invention comprises a sulphonic acid compound or salt thereof of formula:

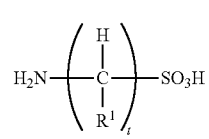

where $R^1$ is H or a $C_{1-10}$ substituted or unsubstituted alkyl group, and t is an integer from 1 to 5.

Preferably the sulphonic acid compound is an amino n-alkyl sulfonic acid, more preferably aminomethanesulfonic acid, 2-aminoethanesulfonic acid (taurine), 3-propane-sulfonic acid (homotaurine), or salts or mixtures thereof. Most preferably the sulphonic acid compound is 2-aminoethanesulfonic acid (taurine).

In an alternative embodiment the sulphonic acid may be thiotaurine.

The weight ratio of DHA to amino acid/peptide is preferably from 1:10 to 10:1, more preferably 1:5 to 5:1, most preferably from 2:1 to 1:2.

Cationic Conditioning Compounds

Compositions of the invention comprise from 0.2 to 10 wt % of the total composition of a cationic conditioning compound. Preferred cationic conditioning compounds are cationic surfactants.

Suitable conditioning surfactants can be used singly or in admixture. Preferably, the cationic surfactants have the formula $N^+R^2R^3R^4$ wherein $R^1$, $R^2$, $R^3$ and $R^4$ are independently ($C_1$ to $C_{30}$) alkyl or benzyl. Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl. More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (eg, oleyl). Alkyl groups are optionally ethoxylated on the alkyl chain with one or more ethyleneoxy groups.

Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant.

Another example of a class of suitable cationic surfactants for use in the invention, either alone or together with one or more other cationic surfactants, is a combination of (i) and (ii) below:
(i) an amidoamine corresponding to the general formula (I):

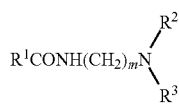

in which $R^1$ is a hydrocarbyl chain having 10 or more carbon atoms,
$R^2$ and $R^3$ are independently selected from hydrocarbyl chains of from 1 to 10 carbon atoms, and m is an integer from 1 to about 10; and
(ii) an acid.

As used herein, the term hydrocarbyl chain means an alkyl or alkenyl chain.

Preferred amidoamine compounds are those corresponding to formula (I) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups.

Preferably, m is 2 or 3, i.e. an ethylene or propylene group.

Preferred amidoamines useful herein include stearamidopropyldimethylamine, stearamidopropyldiethylamine, stearamidoethyldiethylamine, stearamidoethyldimethylamine, palm itamidopropyldimethylamine, palmitamidopropyl-diethylamine, palmitamidoethyldiethylamine, palmitamidoethyldimethylamine, behenamidopropyldimethyl-amine, behenamidopropyldiethylmine, behenamidoethyldiethyl-amine, behenamidoethyldimethylamine, arachidamidopropyl-dimethylamine, arachidamidopropyldiethylamine, arachid-amidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Commercially available amidoamines useful herein include: stearamidopropyldimethylamine with tradenames LEXAMINE S-13 available from Inolex (Philadelphia Pa., USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton N.J., USA).

A protonating acid may be present. Acid may be any organic or mineral acid which is capable of protonating the amidoamine in the conditioner composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, lactic acid and mixtures thereof.

The primary role of the acid is to protonate the amidoamine in the hair treatment composition thus forming a tertiary amine salt (TAS) in situ in the hair treatment composition. The TAS in effect is a non-permanent quaternary ammonium or pseudo-quaternary ammonium cationic surfactant.

Suitably, the acid is included in a sufficient amount to protonate more than 95 mole % (293 K) of the amidoamine present.

The level of cationic surfactant is from 0.2% to 10 wt % more preferably 0.5% to 7.5%, most preferably 1.0% to 5 wt % of the total composition.

Further Ingredients

Compositions of the invention will typically also incorporate a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.01 to 10%, preferably from 0.1% to 8%, more preferably from 0.2% to 7%, most preferably from 0.3% to 6% by weight of the composition. The weight ratio of cationic surfactant to fatty alcohol is suitably from 1:1 to 1:10, preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

In some instance the fatty alcohol can be substituted for fatty (8 to 22 carbon atoms) acid.

i) Silicone Conditioning Agents

The compositions of the invention can contain, emulsified droplets of a silicone conditioning agent, for enhancing conditioning performance. Silicone conditioning agents may be present in the shampoo or conditioner.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the emulsified silicone itself (not the emulsion or the final hair conditioning composition) is typically at least 10,000 cst at 25° C. the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the shampoo compositions of the invention will typically have an average silicone droplet size in the composition of less than 30, preferably less than 20, more preferably less than 10 µm, ideally from 0.01 to 1 µm. Silicone emulsions having an average silicone droplet size of ≤0.15 µm are generally termed microemulsions.

Emulsified silicones for use in the conditioner compositions of the invention will typically have an size in the composition of less than 30, preferably less than 20, more preferably less than 15. Preferably the average silicone droplet is greater than 0.5 µm, more preferably greater than 1 µm, ideally from 2 to 8 µm.

Silicone particle size may be measured by means of a laser light scattering technique, for example using a 2600D Particle Sizer from Malvern Instruments.

Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of silicones for inclusion in shampoos and conditioners of the invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone", Specific examples of amino functional silicones suitable for use in the invention are the aminosilicone oils DC2-8220, DC2-8166 and DC2-8566 (all ex Dow Corning).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

With some shampoos it is preferred to use a combination of amino and non amino functional silicones The total amount of silicone is preferably from 0.01 wt % to 10% wt of the total composition more preferably from 0.1 wt % to 5 wt %, most preferably 0.5 wt % to 3 wt % is a suitable level, especially for a shampoo composition.

(ii) Non-Silicone Oily Conditioning Components

Compositions according to the present invention may also comprise a dispersed, non-volatile, water-insoluble oily conditioning agent. Preferably such non-silicone conditioning oily conditioning agents are present in conditioner compositions. By "insoluble" is meant that the material is not soluble in water (distilled or equivalent) at a concentration of 0.1% (w/w), at 25° C.

Suitable oily or fatty materials are selected from hydrocarbon oils, fatty esters and mixtures thereof. Straight chain hydrocarbon oils will preferably contain from about 12 to about 30 carbon atoms. Also suitable are polymeric hydrocarbons of alkenyl monomers, such as $C_2$-$C_6$ alkenyl monomers.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used.

Suitable fatty esters are characterised by having at least 10 carbon atoms, and include esters with hydrocarbyl chains derived from fatty acids or alcohols, Monocarboxylic acid esters include esters of alcohols and/or acids of the formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Particularly preferred fatty esters are mono-, di- and triglycerides, more specifically the mono-, di-, and tri-esters of glycerol and long chain carboxylic acids such as $C_1$-$C_{22}$ carboxylic acids. Preferred materials include cocoa butter, palm stearin, sunflower oil, soyabean oil and coconut oil.

The oily or fatty material is suitably present at a level of from 0.05 wt % to 10 wt %, preferably from 0.2 wt % to 5 wt %, more preferably from about 0.5 wt % to 3 wt %.

Method of Use

A method of colouring hair comprising the steps of applying to hair a composition comprising dihydroxyacetone or a derivative and
a sulphonic compound of formula:

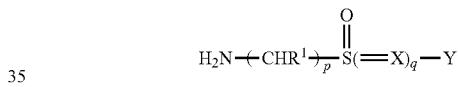

in which where p is an integer from 1 to 5,
$R^1$ is H or an alkyl group,
X is O or S
q is an integer from 0 or 1.
Y is an alkyl group or hydroxyl group.

The level of each composition applied to the head of hair is preferably from 5 g to 100 g.

The composition may be used as a single treatment to colour the hair or applied in a progressive manner so the hair colour becomes more intense on subsequent applications.

Preferably the water used to wet and rinse the hair contains less than 1 ppm of chlorine based bleaching agents such as chlorine dioxide or hypochlorite. Most preferably less than 50 ppb.

The invention will now be illustrated by the following non-limiting examples:

Examples

Hair switches (ex Hiking Group Shandong Haichuan Keeroyal Hair Products Co., Ltd) were bleached by 27% hydrogen peroxide solution (pH=8-8.5) at 35° C. for 16 hours.

TABLE 1

| Experiment | DHA (wt %) | Glycine (wt %) | Taurine (wt %) | S-Taurine** (wt %) | DI water | HU25 conditioner base* |
|---|---|---|---|---|---|---|
| S1 | 5.0 | — | — | — | To 100 | — |
| S2 | 5.0 | 5.0 | — | — | To 100 | — |

TABLE 1-continued

| Experiment | DHA (wt %) | Glycine (wt %) | Taurine (wt %) | S-Taurine** (wt %) | DI water | HU25 conditioner base* |
|---|---|---|---|---|---|---|
| S3 | 5.0 | — | 5.0 | — | To 100 | — |
| S4 | 5.0 | — | — | 5.0 | To 100 | — |
| C1 | 5.0 | — | — | — | — | To 100 |
| C2 | 5.0 | 5.0 | — | — | — | To 100 |
| C3 | 5.0 | — | 5.0 | — | — | To 100 |
| C4 | 5.0 | — | — | 5.0 | — | To 100 |

*conditioner base described in table 2
**S-Taurine: 2-aminoethanethiosulfonic S-acid.

Table 2 Conditioner base formula:

| Tradename | INCI name | Chemical name | Supplier | Conc. (weight %) | Conc. (active %) |
|---|---|---|---|---|---|
| Genamin BTLF | Behenytrimonium Chloride | N,N,N-trimethyldocosan-1-aminium chloride | Clariant | 1.25 | 70 |
| Lexamine S-13 | Steramidopropyl dimethylamine | N-(3-dimethylaminopropyl) octadecanamide | Inolex | 1.25 | 100 |
| Lanette S3 | Cetearyl Alcohol | 14exadecane-1-ol; octadecan-1-ol | Ecogreen Oleo chemicals | 5 | 100 |
| Purac HS-88 | Lactic Acid | 2-hydroxypropanoic acid | Purac | 0.38 | 88 |
|  | Perfume |  | Givaudan | 0.4 | 100 |
| DC 5-7134 9:1 600K/8566 CTAC 70% | Dimethicone/ amodimethicone/ Cetrimonium Chloride | Dimethicone/ amodimethicone/ Cetrimonium Chloride | Dow Corning | 1.79 | 70 |
| Water and minors |  |  | Local | to 100 | 100 |

Hair switches treatment:
1. The hair switch was washed once with surfactant base and the excess water removed.
2. 60 mg of solution (S1 to S4) or conditioner (C1 to C4) was applied to the 300 mg hair switch and massaged for 1.0 minute.
3. The hair switch was dried naturally and left at RT for 24 hours.
4. The treated hair switch was wet using tap water (35-40° C.) followed by application of 30 uL of shampoo base for 30 seconds. The treated hair was rinsed for 30 seconds and excess water removed.
5. Steps 2 to 4 were repeated where necessary.
6. The hair switches were dried naturally.

Photos of treated hair switches were taken by Canon EOS 550D and L*a*b* value recorded by MinoLTA CM-700d Colorimeter. L* means the lightness of the colour. A lower L* value means that the colour is darker.

TABLE 3

Hair colour development

| Experiment | L* of the hair switch | |
|---|---|---|
|  | 1 cycle | 2 cycles |
| S1 | 74.25 ± 1.43 | 73.18 ± 0.71 |
| S2 | 64.59 ± 3.09 | 58.82 ± 1.66 |
| S3 | 64.82 ± 1.53 | 58.84 ± 3.29 |
| S4 | 66.65 ± 1.40 | 59.88 ± 1.54 |
| C1 | 72.96 ± 0.44 | 72.70 ± 0.51 |
| C2 | 67.07 ± 1.53 | 64.56 ± 0.90 |
| C3 | 63.33 ± 0.54 | 61.02 ± 0.62 |
| C4 | 60.43 ± 1.43 | 57.13 ± 0.92 |

Table 3 demonstrates that the examples of the invention colour the hair.

Solution (S1 to S4) and conditioners (C1 to C4) were kept at ambient temperature and 50° C. The stability of the solutions was monitored by UV absorption at 450 nm developed upon storage (Chart 1 and Chart 2). It is reported as Delta Absorption value (DHA alone S1 as control) versus time plot in Chart 1 and Chart 2. The greater the delta absorption value the greater the colour of the product.

TABLE 4

UV absorption of the solutions after storage at 50° C.

| | Delta A @ 450 nm | | |
|---|---|---|---|
| | 3 days | 4 days | 8 days |
| S1 (control) | | | |
| S2 | 0.8732 | 1.2302 | 1.9891 |
| S3 | 0.0005 | 0.0040 | 0.0058 |
| S4 | 0.0279 | 0.0536 | 0.0376 |

TABLE 5

UV absorption of the solutions after storage at ambient temperature

| | Delta A @ 450 nm | | |
|---|---|---|---|
| | 3 days | 4 days | 8 days |
| S1 (Control) | | | |
| S2 | 0.0111 | 0.0217 | 0.0415 |
| S3 | −0.0016 | 0.0018 | 0.0016 |
| S4 | −0.0009 | 0.0034 | 0.0005 |

From tables 4 and 5 it is clear that the stabilities of DHA+Taurine (S3) and DHA+S-Taurine (S4) are much greater than that of DHA+Glycine (S2).

On storage DHA+taurine and DHA+S-taurine conditioner based compositions (C3 and C4) do not turn dark brown on storage at RT for 8 days in contrast example the conditioner formulation with DHA and glycine (C2) is dark brown.

Thus the examples of the invention comprising taurine and S-taurine are much more stable than formulations with DHA+Glycine (C2).

Thus compositions of the invention are stable on storage and effectively colour the hair.

The invention claimed is:

1. A hair colouring composition comprising:
   a) from 0.1 to 15 wt % of the total composition of dihydroxyacetone or a derivative thereof;
   b) from 0.5 to 7.5 wt % of the total composition of a cationic surfactant;
   c) from 0.1 to 15 wt % of the composition of a sulphonic compound of formula:

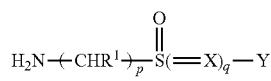

wherein, in the formula for the sulphonic compound,
p is an integer from 1 to 5,
$R^1$ is H or an alkyl group,
X is O or S,
q is an integer from 0 or 1, and
Y is an alkyl group or hydroxyl group; and
d) fatty alcohol,
wherein the weight ratio of cationic surfactant to fatty alcohol is from 1:1 to 1:10 and wherein the composition is in the form of a shampoo or conditioner that includes a lamellar phase in which the cationic surfactant is dispersed.

2. A hair colouring composition according to claim 1 in which the sulphonic compound is of the formula:

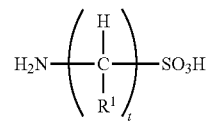

wherein, in formula II $R^1$ is H or $C_1$-$C_{10}$ substituted or unsubstituted alkyl group, and t is an integer from 1 to 5.

3. A composition according to claim 1 in which sulphonic compound is aminomethanesulfonic acid, 2-aminoethanesulfonic acid, 3-propanesulfonic acid, salts or a mixtures thereof.

4. A composition according to claim 1 in which the sulphonic compound is 2-aminoethanesulfonic acid or salt thereof.

5. A composition according to claim 1 in which the sulphonic compound is thiotaurine.

6. A composition according to claim 1 in which the level of sulphonic compound or salt thereof is from 0.5 to 10 wt % of the total composition.

7. A composition according to claim 1 in which the level of dihydroxy acetone is from 0.5 to 10 wt % by weight of the total composition, and the level of cationic surfactant is from 1.0 to 5% by weight of the total composition.

8. A composition according to claim 1 in which the fatty alcohol comprises from 8 to 22 carbon atoms.

9. A composition according to claim 1 in which the composition further comprises a silicone.

10. A method for colouring hair comprising the steps of applying to the hair a composition according to claim 1.

11. A method according to claim 10 that employs subsequent applications of the composition to achieve colouring in a progressive manner.

12. A composition according to claim 1 wherein, wherein the cationic conditioning compound comprises:
   (i) an amidoamine of the formula:

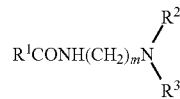

wherein, in the formula for the amidoamine:
$R^1$ is a hydrocarbyl chain having 10 or more carbon atoms,
$R^2$ and $R^3$ are independently selected from hydrocarbyl chains of from
1 to 10 carbon atoms, and m is an integer from 1 to about 10,
in combination with
(ii) an acid.

13. A composition according to claim 1 wherein the weight ratio of cationic surfactant to fatty alcohol is from 1:2 to 1:5.

14. A composition according to claim 12 wherein the acid (ii) protonates the amidoamine (i) and forms a tertiary amine salt in situ in the composition.

* * * * *